United States Patent [19]

Gaffar et al.

[11] 4,110,429
[45] Aug. 29, 1978

[54] ANTIBACTERIAL ORAL COMPOSITION

[75] Inventors: Abdul Gaffar, Somerset; Stuart D. Friedman, Bound Brook, both of N.J.

[73] Assignee: Colgate-Palmolive Company, New York, N.Y.

[21] Appl. No.: 755,895

[22] Filed: Dec. 30, 1976

[51] Int. Cl.$^2$ ............................................. A61K 17/22
[52] U.S. Cl. ...................................................... 424/54
[58] Field of Search .......................................... 424/54

[56] References Cited

U.S. PATENT DOCUMENTS

| | | | |
|---|---|---|---|
| 2,921,885 | 1/1960 | Bouchal | 424/54 |
| 3,703,583 | 11/1972 | Martin | 424/54 |
| 3,758,689 | 9/1973 | Rapfogel | 424/329 |
| 3,864,472 | 2/1975 | Pensak et al. | 424/54 |
| 3,934,002 | 1/1976 | Haefele | 424/54 |
| 3,937,805 | 2/1976 | Harrison | 424/52 |
| 3,937,807 | 2/1976 | Haefele | 424/52 |
| 3,956,480 | 5/1976 | Dichter et al. | 424/54 |
| 3,976,765 | 8/1976 | Nachtigal | 424/54 |
| 3,984,537 | 10/1976 | Harrison et al. | 424/54 |
| 4,025,616 | 5/1977 | Haefele | 424/52 |

OTHER PUBLICATIONS

Chem. Abstr. 72 #112506n of Dannals U.S. 3,498,943 (1970) (Oligomers as Emulsifiers).
Chem. Abstr. 72 #101646g of Dannals et al. Fr. 1,521,995 (1970) (Oligomers Useful As Surfactants, Emulsifiers).

*Primary Examiner*—Shep K. Rose
*Attorney, Agent, or Firm*—Herbert S. Sylvester; Murray M. Grill; Robert L. Stone

[57] ABSTRACT

An antibacterial oral composition effective to promote oral hygiene containing an antibacterial antiplaque agent and an additive which reduces staining of dental surfaces without substantially diminishing the antibacterial and antiplaque activity of the agent. Bis-biguanido hexanes, such as chlorhexidine and alexidine, and quaternary ammonium salts, such as benzethonium chloride and cetyl pyridinium chloride are typical examples of antibacterial agents. The antistain additive is a water soluble oligomer of the formula

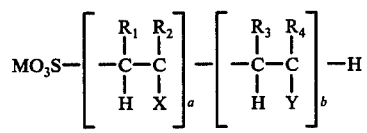

wherein
  M is a water soluble orally acceptable cation;
  $R_1$, $R_2$, $R_3$ and $R_4$ are independently H, methyl or ethyl;
  Y is at least one hydrophilic member of the group consisting of —COOM$_1$, —CONH$_2$, and —CH$_2$OH;
  X is at least one hydrophobic member of the group consisting of —CN, —COOR, —COOR$_5$OR, —CONHR, —COONHR$_5$COR, and —OOCR;
  M$_1$ is H or M;
  R is C$_{1-8}$ alkyl;
  R$_5$ is C$_{1-4}$ alkylene;
  $a$ is 0–7; and
  $a+b$ is about 4–15.

16 Claims, No Drawings

ANTIBACTERIAL ORAL COMPOSITION

This invention relates to an antibacterial oral composition which promotes oral hygiene.

Cationic nitrogen-containing antibacterial materials are well known in the art. See, for instance the section on "Quaternary Ammonium and Related Compounds" in the article on "Antiseptics and Disinfectants" in Kirk-Othmer Encyclopedia of Chemical Technology, second edition (Vol. 2, p. 632–635), incorporated herein by reference. Cationic materials which possess antibacterial activity (i.e. are germicides) are used against bacteria and have been used in oral compositions to counter plaque formation caused by bacteria in the oral cavity.

Among the most common of these antibacterial antiplaque quaternary ammonium compounds is benzethonium chloride, also known as Hyamine 1622 or diisobutylphenoxyethoxyethyl dimethyl benzyl ammonium chloride. In an oral preparation this material is highly effective in promoting oral hygiene by reducing formation of dental plaque and calculus, which is generally accompanied by a reduction in caries formation and periodontal diseases. Other cationic antibacterial agents of this type are those mentioned, for instance, in U.S. Pat. Nos. 2,984,639, 3,325,402, 3,431,208 and 3,703,583, and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, dodecyl dimethyl (2-phenoxyethyl) ammonium bromide, benzyl dimethyl stearyl ammonium chloride, cetyl pyridinium chloride and quaternized 5-amino-1,3-bis (2-ethyl-hexyl)-5-methyl hexa hydropyrimidine are exemplary of other typical quaternary ammonium antibacterial agents.

Other types of cationic antibacterial agents which are desirably incorporated in oral compositions to promote oral hygiene by reducing plaque formation are the amidines such as the substituted guanidines e.g. chlorhexidine and the corresponding compound, alexidine, having 2-ethylhexyl groups instead of chlorophenyl groups and other bis-biguanides such as those described in German patent application No. P 2,332,383 published Jan. 10, 1974, which sets forth the following formula:

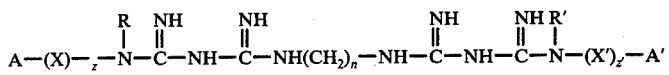

in which A and A' signify as the case may be either (1) a phenyl radical, which as substituent can contain up to 2 alkyl or alkoxy groups with 1 up to about 4C-atoms, a nitro group or a halogen atom, (2) an alkyl group which contains 1 to about 12C-atoms, or (3) alicyclic groups with 4 to about 12C-atoms, X and X' as the case may be may represent an alkylene radical with 1–3C atoms, $z$ and $z'$ are as the case may be either zero or 1, R and R' as the case may be may represent either hydrogen, an alkyl radical with 1 to about 12C-atoms or an aralkyl radical with 7 to about 12C-atoms, $n$ is a whole number of 2 to inclusively 12 and the polymethylene chain ($CH_2$) can be interrupted by up to 5 ether, thioether, phenyl- or naphthyl groups; these are available as pharmaceutically suitable salts. Additional substituted guanidines are: N'-(4-chlorobenzyl)-$N^5$-(2,4-dichlorobenzyl) biguanide; p-chlorobenzyl biguanide, 4-chlorobenzhydryl guanylurea; N-3-lauroxypropyl-$N^5$-p-chlorobenzyl biguanide; 5,6-dichloro-2-guanidobenzimidazole; and N-p-chlorophenyl-$N^5$-laurylbiguanide.

The long chain tertiary amines also possess antibacterial and antiplaque activity. Such antibacterial agents include tertiary amines having one fatty alkyl group (typically 12 to 18 carbon atoms) and 2 poly(oxyethylene) groups attached to the nitrogen (typically containing a total of from 2 to 50 ethenoxy groups per molecule) and salts thereof with acids and compounds of the structure:

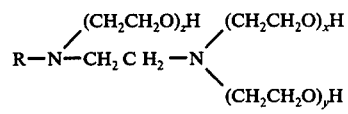

where R is a fatty alkyl group containing 12 to 18 carbon atoms and $x$, $y$ and $z$ total 3 or higher, as well as salts thereof. Generally, cationic agents are preferred for their antiplaque effectiveness.

The antibacterial antiplaque compound is preferably one which has an antibacterial activity such that its phenol co-efficient is well over 50, more preferably well above 100, such as above about 200 or more for S. aureus; for instance the phenol coefficient (A.O.A.C.) of benzethonium chloride is given by the manufacturer as 410, for S. aureus. The cationic antibacterial agent will generally be a monomeric (or possibly dimeric) material molecular weight well below 2,000, such as less than about 1,000. It is, however, within the broader scope of the invention to employ a polymeric cationic antibacteria agent. The cationic antibacterial is preferably supplied in the form of an orally acceptable salt thereof, such as the chloride, bromide, sulfate, alkyl sulfonate such as methyl sulfonate and ethyl sulfonate, phenylsulfonate, such as p-methylphenyl sulfonate, nitrate, acetate, gluconate, etc.

The nitrogen-containing cationic antibacterial agents and long chain tertiary amine antibacterial agents effectively promote oral hygiene, particularly by removing plaque. However, their use has been observed to lead to staining of dental surfaces or discoloration.

The reason for the formation of such dental stain has not been clearly established. However, human dental enamel contains a high proportion (about 95%) of hydroxyapatite (HAP) which includes $Ca^{+2}$ and $PO_4^{-3}$ ions. In the absence of dental plaque additional $Ca^{+2}$ and $PO_4^{-3}$, particularly from saliva, can be deposited on the enamel and such deposits can include color bodies which ultimately stain the tooth enamel as a calcified deposit thereon. It can be that as the cationic or long chain tertiary amine antibacterial agents remove plaque they also denature protein from saliva in the oral environment and the denatured protein can then act as a nucleating agent which is deposited on and stains or discolors tooth enamel.

Previously employed additives which reduced dental staining by cationic antibacterial antiplaque agents also generally reduced the activity of the antibacterial agents or its ability to act on dental plaque to measurable degrees. Further Victamide (also known as Victamine C) which is the condensation product of ammonia with phosphorus pentoxide actually increases staining even in the absence of a cationic antibacterial antiplaque agent and it and other known phosphorus containing agents such as disodiumethane-1-hydroxy-1,1-diphosphonic acid salt precipitate in the presence of antibacterial agent such as bis-biguanido compound, thereby reducing the antiplaque effectiveness of the antibacterial agent.

It is an advantage of this invention that an antinucleating additive is provided which unexpectedly prevents staining of dental enamel without precipitating or substantially adversely affecting the antibacterial and antiplaque activity of cationic or long chain tertiary amine antibacterial agents. Other advantages will be apparent from consideration of the following disclosure.

In accordance with certain of its aspects, this invention relates to an oral composition comprising an oral (orally acceptable) vehicle, at least one cationic or long chain tertiary amine antibacterial antiplaque agent which causes staining and, as anti-staining additive, at least one water soluble oligomer of the formula:

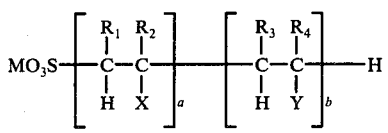

wherein
M is a water soluble orally acceptable cation;
$R_1, R_2, R_3$ and $R_4$ are independently H, methyl or ethyl;
Y is at least one hydrophilic member of the group consisting of $-COOM_1$, $-CONH_2$, and $-CH_2OH$;
X is at least one hydrophobic member of the group consisting of $-CN$, $-COOR$, $-COOR_5OR$, $-CONHR$, $-COONHR_5COR$, and $-OOCR$;
$M_1$ is H or M;
R is $C_{1-8}$ alkyl;
$R_5$ is $C_{1-4}$ alkylene;
$a$ is 0–7; and
$a+b$ is about 4–15.

Oligomers of the above formula and methods for their production are disclosed in U.S. Pat. Nos. 3,646,099 and 3,859,260, which disclosures are incorporated herein by reference thereto. These oligomers of relatively low and accurately regulated degree of polymerization, [in contrast to the conventional free radical redox polymerization conducted with an oxidative initiator such as hydrogen, alkyl, or acyl peroxides, persulfates or hydroperoxides in relatively large amounts and a reductive activator such as $NaHSO_3$, $Na_2S_2O_3$, $Na_2S_2O_4$ or sodium formaldehyde sulfoxylate in relatively low amounts generally added subsequently to the polymerization medium] are prepared by a reductive polymerization in which a much larger amount of a bisulfite salt, e.g. $NaHSO_3$ (sodium bisulfite, sodium acid sulfite), a reducing agent, is the initiator charged initially with the monomer, and an oxidizing agent is added in smaller amounts as the activator during the polymerizing or oligomerizing process.

Subscript $a$ in formula I represents the number of moles of hydrophobic groups, and subscript $b$ the number of moles of hydrophilic groups, in the oligomer molecule. The proportion of X (i.e. the value of $a$) must be small enough, or even zero, to avoid the production of a too large, sticky, and hydrophobic polymer molecule, and will of course be dependent for the most part in any particular instance on the identity of the X and Y groups, i.e. the hydrophobic-containing and hydrophilic-containing monomeric reactants. Mixtures of such oligomers may of course also be employed.

Examples of monomers containing hydrophilic Y groups are acrylic acid, methacrylic acid, alpha-ethylacrylic acid, beta-methylacrylic acid, alpha, beta-dimethylacrylic acid, orally acceptable salts ($M_1$) of these acids, for example those containing such cations as alkali metal (e.g. sodium and potassium), ammonium, $C_{1-18}$ mono-, di- and tri- substituted ammonium (e.g. alkanol substituted such as mono-, di- and tri-ethanolammonium), etc., acrylamide, methacrylamide, ethacrylamide, and allyl alcohol and the like.

Examples of monomers containing hydrophobic X groups are acrylonitrile, methacrylonitrile, ethacrylonitrile, methyl and ethyl and octyl acrylate and methacrylate, methoxyethyl acrylate, octoxyethyl methacrylate, ethoxybutyl methacrylate, propoxymethyl acrylate, N-ethylacrylamide, N-isopropylacrylamide, N-methylacrylamide, N-isooctylmethacrylamide, N-propylethacrylamide, vinyl acetate, propionate and octanoate, diacetone acrylamide and the like.

The oligomerization is carried out in water in the presence of a relatively large amount of the bisulfite reducing initiator. Generally, the amount of reducing initiator, expressed in mols of monomer/gram formula weight (gFW) of reducing initiator is about 4 to 15, this ratio determining the degree of oligomerization.

The reductive initiator is preferably a water soluble bisulfite salt, (M in formula I), especially alkali metal such as sodium or potassium, but bisulfite salts containing other orally acceptable cations of the type referred to above may be employed.

In practice, enough oxidative activator is used to effect 100% conversion of the monomers to oligomers. The amount of such activator, expressed as gFW activator/gFW initiator may range from 0.0001 to 0.1 but usually is from about 0.001 to 0.1. Examples of these oxidative activators are ammonium, sodium and potassium persulfate, hydrogen peroxide and other water soluble oxidants commonly employed in the polymerization art.

Following completion of the oligomerization reaction, any free carboxylic acid groups in the oligomer molecules may if desired be partially or completely neutralized, preferably at least 60%, by treating the aqueous oligomer solution with a suitable base to convert such groups to their salts with orally acceptable cations as referred to above. These aqueous oligomer solutions have a highly desirable low viscosity, and low molecular weight range depending on the monomer units in the oligomer.

It will be understood that Formula I above is not intended to depict the actual structure of the oligomer molecule, the bracketed units of which formula are randomly distributed in the molecule with the $-SO_3M$ group being normally bonded to a terminal carbon atom in the oligomer chain devoid of X and or Y substituents. In the oligomers preferred for use herein, $a$ is zero, Y is $-COOM_1$, $R_1-R_4$ are H, and M and $M_1$ are alkali metal, e.g. sodium, $b$ being about 10, as derived from acrylic acid. An oligomer of formula I above in the form of its sodium salt, with a molecular weight of about 1,000, containing about 10 acrylic acid monomeric units, is commercially available under the trade name ND-2 (a product of UniRoyal).

U.S. Pat. No. 3,934,002, discloses among a number of alternative compounds suggested for reducing the staining ordinarily caused by bis-biguanide antiplaque agents, homopolymers and copolymers containing units of the type present in the oligomer additives of this invention. Such polymers however are devoid of the essential sulfonic group of said oligomers, and are difficult to produce in the low 4–15 unit range and low-viscosity properties attributable to such oligomers. Such oligomers are further more advantageously employed in the instant oral compositions by reason of their water-solubilizing, water-dispersing sulfonic acid substituents.

The concentration of these oligomer additives in oral compositions can range widely, typically upward from about 0.01% by weight with no upper limit except as dictated by cost or incompatibility with the vehicle. Generally, concentrations of about 0.01% to about 10% and preferably about 0.5% to 2% by weight are utilized. Oral compositions which in the ordinary course of usage could be accidentally ingested preferably contain lower concentrations of these additives. Thus, a mouthwash in accordance with this invention preferably contains less than about 1 weight % of the additive. Dentrifice compositions, topical solutions and prophylactic pastes, the latter to be administered professionally, can preferably contain about 0.1 to 2 weight % of the additive. Most desirably the oligomer additive is present in a molar ratio relative to the amount of antibacterial antiplaque agent (based on its free base form) of about 0.2:1 to about 6:1, preferably about 0.5:1 to about 4:1, in order to best minimize, inhibit or prevent staining.

Nitrogen-containing antibacterial agents which are cationic or long chain amine germicides which may be employed in the practice of this invention are described above. They are typically employed in amounts such that the oral product contains between about 0.001 and 15% by weight of the agent. Preferably for desired levels of antiplaque effect, the finished oral product contains about 0.01 to about 5%, and most preferably about 0.25 to 1.0% by weight of the antibacterial agent, referring to its free base form.

The stain which generally occurs on dental enamel is unexpectedly substantially or entirely prevented when the above-defined oligomer additives or orally acceptable water soluble salts thereof, are employed. These materials are anti-nucleating agents. In themselves (even in the absence of cationic antiplaque antibacterial agents) they are effective to reduce formation of dental calculus without unduly decalcifying enamel. However, not all anti-nucleating agents are effective to prevent stain by cationic antibacterial agents. Victamide actually increases staining even in the absence of an antibacterial antiplaque agent.

In certain highly preferred forms of the invention the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying dental enamel.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 cm$^2$/gm. silica gel, complex amorphorus alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37 %, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner, as illustrated by Thorpe's *Dictionary of Applied Chemistry*, Volume 9, fourth Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 20 to about 99% by weight of the oral preparation. Preferably, it is present in amounts ranging from about 20 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antibacterial antiplaque agent and oligomer additive should be compatible with the other components of the preparation. Thus, in a toothpaste, the liquid vehicle may comprise water and humectant typically in an amount ranging from about 10 to about 90% by weight of the preparation. Glycerine, sorbitol, or polyethylene glycol may also be present as humectants or binders. Particularly advantageous liquid ingredients comprise mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gumlike materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to about 10% by weight, preferably in the range of from about 0.5 to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0, may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

In oral compositions such as mouthrinses and toothpastes, a surfactant is often present, e.g. to promote foaming. It will be understood that it is preferable to employ nonionic surfactants rather than their anionic counterparts. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of ethylene oxide with fatty acids, fatty alcohols, and fatty amides, including alcohols such as sorbitan monostearate or polypropyleneoxide (that is Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013 to 0.1% and most preferably about 0.0013 to 0.05%, by weight, of fluoride ion.

Various other materials may be incorporated in the oral preparations of this invention. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and saccharine. Suitably, flavor and sweetening agents may together comprise from about 0.01 to 5% or more of the preparation.

In preparing the oral compositions of this invention comprising the above-defined combination of antibacterial agent and oligomer additive in an oral vehicle which typically includes water, it is highly preferred if not essential to add the oligomer after the other ingredients (except perhaps some of the water) are mixed or contacted with each other to avoid a tendency for said agent to be precipitated.

For instance, a mouthrinse or mouthwash may be prepared by mixing ethanol and water with flavoring oil, nonionic surfactant, humectant, cationic antibacterial antiplaque agent, such as benzethonium chloride or chlorohexidine, sweetener, color and then the above-defined oligomer additive, followed by additional water as desired.

A toothpaste may be prepared by forming a gel with humectant, gum or thickener such as hydroxyethyl cellulose, sweetener and adding thereto polishing agent, flavor, antibacterial agent, such as benzethonium chloride or chlorhexidine, additional water, and then the above-defined oligomer additive. If sodium carboxymethyl cellulose is employed as the gelling agent the procedure of either U.S. Pat. No. 3,842,168 or U.S. Pat. No. 3,843,779, modified by the inclusion of the oligomer additive, is followed.

In the practice of this invention an oral composition according to this invention such as a mouthwash or toothpaste containing cationic or long chain amine antibacterial antiplaque agent in an amount effective to promote oral hygiene and the defined oligomer additive in an amount effective to reduce staining of dental surfaces otherwise resulting from the presence of the antibacterial antiplaque agent, is applied regularly to dental enamel, preferably from about 5 times per week to about 3 times daily, at a pH of about 4.5 to about 9, generally about 5.5 to about 8, preferably about 6 to 8.

The following specific examples are further illustrative of the nature of the present invention, but it is understood that the invention is not limited thereto. All amounts and proportions referred to herein and in the appended claims are by weight unless otherwise indicated.

EXAMPLE A

The procedure of Example 1 of U.S. Pat. No. 3,646,099 is followed, the initial charge to the reactor being 3.12g NaHSO$_3$ (0.03 gFW), 159.8g. water, and 20.74g. acrylic acid (0.288 mol) as the sole monomer, a correspondingly equivalent amount of the (NH$_4$)$_2$S$_2$O$_8$ activator being employed. The ratio of mols of monomer to gFW NaHSO$_3$ is 9.6, and the oligomer, fully neutralized with 5NNaOH at the completion of the reaction, may be represented by the formula

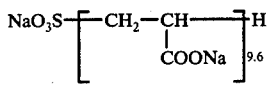   A

In this case, $a$ in formula I above is zero and $b$ is 9.6 (average). A clear solution is obtained, this Oligomer A having a molecular weight of about 1,000.

EXAMPLE 1

Inhibition of Crystal Growth of HAP

This is evaluated by a pH Stat method. 1.0 ml of 0.1M sodium dihydrogen phosphate is placed in a reaction flask with 22 to 23 ml. of distilled water with continuous stirring in an atmosphere of nitrogen. To this is added 1 ml. of 0.1M CaCl$_2$ and the pH adjusted to 7.4±0.05 (final conc. of Ca$^{++}$ and PO$_4^{3-}$ —4×10$^{-3}$M). Consumption of 0.1MNaOH is recorded automatically by a pH Stat (Radiometer). In this test, the formation of HAP occurs in 2 distinct phases. First rapid base consumption (1–4 min.) then diminishes until 15–20 minutes when second rapid uptake takes place. A delay in the time of second rapid consumption or a total absence of the second rapid consumption indicates an interference with the crystal growth of HAP. Agents which interfere with HAP crystal growth are effective anticalculus agents. When subjected to the foregoing procedure, Oligomer A above is found to delay the formation of the second phase by more than 12 hours, while Acrysol A-5 polyacrylic acid and sodium polyacrylic acid have no affect.

It is thus clear that Oligomer A effectively inhibits the crystal growth of HAP and that the inhibition is not merely due to the complexation or chelation of calcium from the system since the ratio of inhibitor to total calcium is 1:40 to 1:80.

In the following examples, BC refers to benzethonium chloride, and Pluronic F108 is a polyalkene oxide block polymer.

TABLE I

| | MOUTHWASH FORMULATIONS | | | | |
|---|---|---|---|---|---|
| Example | (1) Placebo | (2) Control | (3) | (4) | (5) |
| Flavor | 0.22% | 0.22% | 0.22% | 0.22% | 0.22% |
| Ethanol | 15.0 | 15.0 | 15.0 | 15.0 | 15.0 |
| Pluronic F108 | 3.0 | 3.0 | 3.0 | 3.0 | 3.0 |
| Glycerine | 10.0 | 10.0 | 10.0 | 10.0 | 10.0 |
| Na saccharin | 0.03 | 0.03 | 0.03 | 0.03 | 0.03 |
| BC | — | 0.075 | 0.075 | 0.075 | 0.075 |
| Oligomer A | — | — | 0.1 | 0.2 | 0.5 |
| Water q.s. to | 100 | 100 | 100 | 100 | 100 |
| pH(with NaOH) | 7.4 | 7.4 | 7.4 | 7.4 | 7.4 |
| Appearance | Clear | Clear | Clear | Clear | Clear |
| Reflectance | 55.0 | 46.0 | 53.0 | 54.0 | 54.0 |
| Reflectance Difference | — | — | 7.0 | 8.0 | 8.0 |

The Oligomer A and about 10 parts of the water are added to the other previously mixed ingredients. Tooth staining characteristics are tested by slurrying hydroxyapatite (Biogel) with salivary protein, acetaldehyde (as carbonyl source) and a pH7 phosphate buffer. The mixture is shaken at 37° C. until a light brown color is formed. Colored powder is separated by filtration, dried and color levels (in reflectance units) determined on a Gardner color difference meter before and after the test formulation is applied to the colored material.

The above results plainly establish that the oligomer additives of the present invention, as exemplified by Oligomer A, substantially reduce dental staining ordinarily produced by quaternary ammonium antibacterial antiplaque agents as exemplified by BC. Formulations adjusted to pH5–8 yield similar results. Other orally acceptable salts of Oligomer A yield similar results.

Further, In vitro tests for antiplaque activity against a preformed plaque on teeth (induced by *Actinomyces viscosus*) establish the formulation of Example 2 (0.075%BC) and a similar formulation also containing 1.0% of Oligomer A to be substantially equal, indicating that these oligomer additives do not significantly affect the antiplaque activity of BC and the like.

Substitution of equivalent amounts of the following antibacterial antiplaque agents for the BC employed in Examples 3–5 yield formulations also producing unexpected reductions in dental staining:

| Example | Antibacterial Antiplaque Agent |
|---|---|
| 6 | chlorhexidine diacetate |
| 7 | chlorohexidine digluconate |
| 8 | dodecyl trimethyl ammonium bromide |
| 9 | cetyl pyridinium chloride |

-continued

| Example | Antibacterial Antiplaque Agent |
|---------|-------------------------------|
| 10 | $C_{12-18}$ alkyl $-N-CH_2CH_2N\begin{matrix}CH_2CH_2OH\\CH_2CH_2OH\\CH_2CH_2OH\end{matrix}$ with $CH_2CH_2OH$ |
| 11 | alexidine dihydrochloride |

The following formulations exemplify toothpastes with antiplaque activity and reduced staining:

| | Example (Parts) | |
|---|---|---|
| | 12 | 13 |
| Hydrated alumina | 30 | 30 |
| Glycerine | 16 | 16 |
| Sorbitol (70%) | 6 | 6 |
| Pluronic F-108 | 3 | 3 |
| Hydroxyethyl cellulose | 1.2 | 1.2 |
| Benzethonium chloride (BC) | 0.5 | — |
| Chlorhexidine digluconate (20%) | — | 4.725 |
| Oligomer A | 2 | 2 |
| Sodium saccharin | 0.17 | 0.17 |
| Flavor | 0.8 | 0.8 |
| Water q.s. to | 100 | 100 |

Significant reductions in dental staining are also obtained according to the present invention when Oligomer A in the above examples is replaced by any of the co-oligomers prepared by the procedures of Examples I-XIII of U.S. Pat. Nos. 3,646,099 and 3,859,260 suitably adjusted to yield a co-oligomer of formula I above in which $a$ is 0-7 and $a+b$ is about 4-15.

This invention has been described with respect to preferred embodiments and it will be understood that modifications and variations thereof obvious to those skilled in the art are to be included within the spirit and purview of this application and the scope of the appended claims.

What is claimed is:

1. An oral composition comprising an oral vehicle, at least one nitrogen-containing antibacterial antiplaque agent, whose use has been observed to lead to staining or discoloration of dental surfaces, selected from the group consisting of cationic antibacterial antiplaque agent and long chain amine antibacterial antiplaque agent containing a fatty alkyl group of about 12 to 18 carbon atoms and as an anti-staining additive, present in a molar ratio, relative to said agent, of about 0.2:1 to about 6:1, of at least one water soluble oligomer of the formula $$MO_3S-\left[\begin{matrix}R_1 & R_2\\ -C-C-\\ H & X\end{matrix}\right]_a - \left[\begin{matrix}R_3 & R_4\\ -C-C-\\ H & Y\end{matrix}\right]_b -H$$

wherein

M is a water soluble orally acceptable cation;

$R_1, R_2, R_3$ and $R_4$ are independently H, methyl or ethyl;

Y is at least one hydrophilic member of the group consisting of $-COOM_1$, $-CONH_2$, and $-CH_2OH$;

X is at least one hydrophobic member of the group consisting of $-CN$, $-COOR_5OR$, $-CONHR$, $-COONHR_5COR$, and $-OOCR$;

$M_1$ is H or M;

R is $C_{1-8}$ alkyl;

$R_5$ is $C_{1-4}$ alkylene;

$a$ is 0-7; and $a+b$ is about 4-15.

2. The oral composition of claim 1 wherein said antibacterial antiplaque agent is present in an amount to provide about 0.001 to about 15% by weight based on the free base form of said agent and said oligomer is present in amount of about 0.01 to about 10% by weight.

3. The oral composition of claim 2 wherein said antibacterial antiplaque agent is present in an amount of about 0.01 to about 5% by weight, based on its free base form.

4. The oral composition of claim 2 wherein said antibacterial antiplaque agent is a substituted guanidine.

5. The oral composition of claim 4 wherein said antibacterial antiplaque agent is a pharmaceutically acceptable water soluble salt of an agent selected from the group consisting of chlorhexidine and alexidine.

6. The oral composition of claim 5 wherein said antibacterial antiplaque agent is a pharmaceutically acceptable water soluble salt of chlorhexidine.

7. The oral composition of claim 2 wherein said antibacterial antiplaque agent is benzethonium chloride.

8. The oral composition of claim 2 wherein said antibacterial antiplaque agent is a quaternary ammonium compound containing 1 to 2 alkyl groups of 8 to 20 carbon atoms.

9. The oral composition of claim 8 wherein said antibacterial antiplaque agent is cetyl pyridinium chloride.

10. The oral composition of claim 1 wherein, in said formula, $a$ is zero, $a+b$ is about 10, Y is $-COOM_1$, $R_1$, $R_2$, $R_3$ and $R_4$ are H, and M and $M_1$ are sodium.

11. The oral composition of claim 1 wherein said vehicle is an aqueous-alcohol and said composition is a mouthwash of pH of about 4.5 to about 9.

12. The oral composition of claim 1 wherein said vehicle comprises a liquid vehicle and a gelling agent and a dentally acceptable polishing material is present and said composition is a toothpaste of pH of about 4.5 to about 9.

13. The mouthwash composition of claim 11 containing about 0.01 to about 5.0% by weight, based on its free base form, of benzethonium chloride.

14. The mouthwash composition of claim 11 containing about 0.01 to about 5% by weight, based on its free base form, of a water-soluble pharmaceutically acceptable salt of chlorhexidine.

15. A method of preparing an oral composition as defined in claim 1 wherein said oligomer is added to the remaining components of said composition after said components have been contacted with each other.

16. A method of improving oral hygiene comprising applying to the oral cavity an effective amount of an oral composition as defined in claim 1.

* * * * *